United States Patent
Dehghan et al.

(10) Patent No.: US 9,744,108 B2
(45) Date of Patent: Aug. 29, 2017

(54) METHODS AND COMPOSITIONS FOR PREVENTING AND TREATING TOOTH EROSION

(71) Applicant: University of Tennessee Research Foundation, Knoxville, TN (US)

(72) Inventors: Mojdeh Dehghan, Germantown, TN (US); Daranee Versluis-Tantbirojn, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 14/771,222

(22) PCT Filed: Feb. 28, 2014

(86) PCT No.: PCT/US2014/019447
§ 371 (c)(1),
(2) Date: Aug. 28, 2015

(87) PCT Pub. No.: WO2014/134463
PCT Pub. Date: Sep. 4, 2014

(65) Prior Publication Data
US 2016/0000664 A1    Jan. 7, 2016

Related U.S. Application Data

(60) Provisional application No. 61/770,863, filed on Feb. 28, 2013.

(51) Int. Cl.
| | |
|---|---|
| A61K 8/21 | (2006.01) |
| A61K 8/24 | (2006.01) |
| A61K 8/20 | (2006.01) |
| A61K 8/41 | (2006.01) |
| A61K 8/19 | (2006.01) |
| A61K 8/97 | (2017.01) |
| A61Q 11/00 | (2006.01) |

(52) U.S. Cl.
CPC ............. *A61K 8/21* (2013.01); *A61K 8/19* (2013.01); *A61K 8/20* (2013.01); *A61K 8/24* (2013.01); *A61K 8/41* (2013.01); *A61K 8/97* (2013.01); *A61Q 11/00* (2013.01); *A61K 2800/20* (2013.01)

(58) Field of Classification Search
USPC .................................................... 424/52, 401
See application file for complete search history.

(56) References Cited

U.S. PATENT DOCUMENTS

| 4,080,440 A | 3/1978 | DiGiulio et al. |
| 4,367,218 A | 1/1983 | Jacobson |
| 4,606,912 A * | 8/1986 | Rudy ..................... A61K 8/19 |
| | | 424/52 |
| 5,738,840 A | 4/1998 | Richter |
| 5,833,957 A | 11/1998 | Winston et al. |
| 6,159,448 A | 12/2000 | Winston et al. |
| 2008/0075675 A1 | 3/2008 | Reynolds |

FOREIGN PATENT DOCUMENTS

| WO | 2011068813 A1 | 6/2011 |
| WO | 2012143220 A1 | 10/2012 |

OTHER PUBLICATIONS

Hurlbutt et al., "Dental Caries: A pH-mediated disease." CDHA Journal—Winter 2010; pp. 9-15.*
International Search Report and Written Opinion of the International Searching Authority, dated of mailing Jun. 6, 2014, of International PCT Application No. PCT/US2014/019447 filed Feb. 28, 2014.

* cited by examiner

*Primary Examiner* — Walter Webb
(74) *Attorney, Agent, or Firm* — Sorell, Lenna & Schmidt LLP; William D. Schmidt, Esq.

(57) ABSTRACT

Methods and compositions are provided for reducing, treating or preventing dental erosion in a patient in need of such treatment, the methods and compositions comprising administering a therapeutically effective amount of an alkalinizing agent and a re-mineralizing agent to the teeth. Dental erosion is a significant oral health problem that affects millions of individuals around the world. Erosive tooth wear can cause significant tooth damage compromising the esthetics and function of teeth, requiring extensive dental treatment.

8 Claims, 3 Drawing Sheets

METHODS AND COMPOSITIONS FOR PREVENTING AND TREATING TOOTH EROSION

This application claims priority to U.S. Provisional Application Ser. No. 61/770,863, filed Feb. 28, 2013, entitled "Methods and Compositions For Preventing and Treating Tooth Erosion". This application is incorporated herein by reference into the present disclosure.

FIELD

The present invention relates to methods and compositions for preventing and treating tooth erosion.

BACKGROUND

Dental erosion is a significant oral health problem that affects millions of individuals around the world. Erosive tooth wear can cause significant tooth damage compromising the esthetics and function of teeth, requiring extensive dental treatment. Typically, dental erosion is caused by direct contact of intrinsic or extrinsic acid exposure to natural tooth enamel. Erosive tooth wear is a form of chemical tooth loss that causes enamel dissolution without involvement of bacterial origin. (Imfeld, 1996). Oral health problems associated with dental erosion of teeth have become more prevalent in recent years due to the popularity of diets high in acidic contents, increase in use of medication causing low salivary flow and systemic conditions such as gastro esophageal reflux disease (GERD) and Bulimia. Erosion no longer affects only the elderly population but can manifest in all age groups of our society. Acids either from intrinsic or extrinsic origin can soften tooth enamel. Softening of the enamel surface is an early manifestation of acid erosion. Subsequently, the tooth structures are dissolved layer by layer or by a mechanical insult, resulting in bulk-loss of tooth material.

Erosive tooth wear from hydrochloric acid when stomach juice is involuntarily regurgitated has been associated with chronic health issues such as in GERD, hiatal hernia, or occur through chronic vomiting like in bulimia nervosa (Schroeder et al., 1995; Valena and Young, 2002; Barron et al., 2003). Prevalence of dental erosion in GERD patients is approximately 24% (Pace et al., 2008). According to the National Eating Disorders Association, approximately 11 million Americans suffer from eating disorders. (Eating Disorders and their Precursors, www.NationalEatingDisorders.org 2005). Moderate to advanced erosion and tooth wear present on the lingual and incisal edges of a patient's upper anterior teeth are manifestations of a systemic condition such as Bulimia and GERD. The majority of these patients require extensive restorative work to return the teeth to optimal function and esthetics.

Various products containing fluoride and/or calcium phosphate are readily available for caries prevention. Many of these products also address the re-mineralization of teeth by providing fluoride as a rinse or gel, but none of the products available address neutralizing the acidity of saliva, which is the natural medium of teeth. Preventive treatments that can reduce tooth damage from hydrochloric acid erosion will certainly benefit patients suffering from acid erosion of the teeth (e.g., patients suffering from GERD, eating disorders, drinking excessive amounts of acidic drinks, etc.)

Accordingly, there is a need for compositions and methods to prevent and treat tooth erosion in patients exhibiting tooth damage. Compositions and methods are needed to re-harden and re-mineralize the teeth. Patients suffering from conditions such as GERD or Bulimia are in need of compositions and methods for treating tooth erosion.

SUMMARY

New compositions and methods are provided that effectively prevent, treat and reduce tooth erosion in patients suffering from conditions that increase the acidity in the oral cavity, such as GERD and Bulimia.

In one embodiment, a method is provided for treating or preventing erosion of the teeth in a patient in need of such treatment, the method comprising applying a therapeutically effective amount of an alkalinizing agent to the teeth so as to raise saliva pH to 7.0 or above, and to re-harden tooth enamel; and applying a therapeutically effective amount of a re-mineralizing agent to the teeth.

In an exemplary embodiment, a method is provided for treating or preventing erosion of the teeth in a patient in need of such treatment, the method comprising applying a therapeutically effective amount of an alkalinizing agent, wherein the alkalinizing agent comprise an alkalinizing mouthwash; and applying a therapeutically effective amount of a re-mineralizing agent, wherein the re-mineralizing agent comprises a re-mineralizing mouthwash.

In another embodiment, a kit is provided for treating or preventing erosion of the teeth in a patient in need of such treatment, the kit comprising a first composition comprising a therapeutically effective amount of an alkalinizing agent to raise saliva pH to 7.0 or above and a re-hardening agent to re-harden the enamel on the teeth; and a second composition comprising a therapeutically effective amount of re-mineralizing agent the teeth.

In another embodiment, a composition is provided for neutralizing saliva and re-hardening tooth enamel, the composition comprising an alkalinizing mouthwash comprising a therapeutically effective amount of an alkalinizing agent so as to raise the pH of the saliva to 7.0 or greater, and further comprising a therapeutically effective amount of a re-hardening agent so as to re-harden the tooth enamel.

In another embodiment, a composition is provided for re-mineralizing the teeth, the composition comprising a therapeutically effective amount of re-mineralizing mouthwash comprising a therapeutically effective amount of calcium, phosphate and fluoride.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1A:
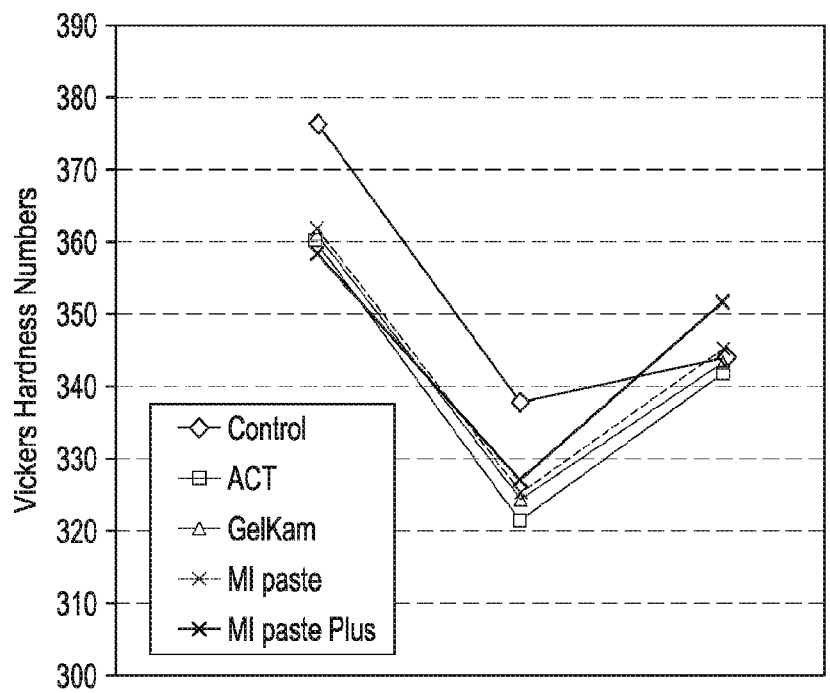
FIGS. 1A and 1B illustrate the effect of various formulations on the hardness recovery of softened tooth enamel.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an alkalinizing agent" includes one, two, three or more alkalinizing agents.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Alkalinizing Agent

Alkalinizing agents are useful for neutralizing acids of the oral cavity. Alkalinizing agents can buffer the acids in the mouth and raise pH levels in acidic saliva from as low as 1.0 to 6.8 or greater. For example, treatment can be started when saliva pH is about 1.0, 1.5, 2.0, 2.5, 3.0, 3.5, 4.0, 4.5 or 5.0. The process of using an alkalinizing agent is useful for preventing and treating tooth erosion. Examples of alkalinizing agents include, but are not limited to, arginine, sodium carbonate, sodium bicarbonate, potassium carbonate, potassium bicarbonate, calcium carbonate, calcium bicarbonate, sesquicarbonates, borates, silicates, phosphates (e.g., monosodium phosphate, trisodium phosphate, pyrophosphate salts, etc.), imidazole or combinations thereof.

Saliva is a naturally occurring alkalinizing agent. Salivation is enhanced by agents stimulating the salivary glands. Saliva is the most significant natural defense in the oral cavity and is well known to possess several tooth-protective properties including antibacterial action, buffering capacity, cleansing effect, and re-mineralization activity.

In some embodiments, the alkalinizing agents may also comprise licorice root, *eucalyptus* or arginine from about 1%, 2%, 3%, 4%, 5%, 6%, 7% or to about 8%.

Alkalinizing agents may also comprise a re-hardening agent and buffering agent. Re-hardening of tooth enamel occurs when an agent capable of hardening tooth enamel is applied to the teeth after an acidic challenge to the teeth, which softens the enamel. Re-hardening agents are substances which are applied to the teeth to harden the softened enamel. Examples of re-hardening agents include, but are not limited to, green tea extract, calcium phosphate, fluoride, sodium fluoride, stannous fluoride, calcium chloride, potassium phosphate, casein phosphopeptide, caseinates, digests thereof or casein-derived phosphopeptides, amorphous calcium phosphate or combinations thereof. Enamel re-hardening is indicative of the effectiveness of various preventive treatments.

In some embodiments, the alkalinizing agent discussed above can be in the composition from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the alkalinizing agent can raise the pH of saliva to above about 6.0, 6.5, 7.0, 7.5, 8.0, 8.5, 9.0, to about 9.5 or higher if desired.

In some embodiments, the rehardening agents can be in the composition from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, buffering agents include sodium chloride, 4-(2-hydroxyethyl)-1-piperazineethanesulfonic acid (HEPES), potassium hydroxide, potassium chloride, carboxylic, phosphoric and sulfonic acids, acid salts (e.g., monosodium citrate, disodium citrate, monosodium malate, etc.) or combinations thereof. Buffering agents can be added to the composition at concentrations of about 1 mM to about 300 mM. Buffering agents are added in sufficient quantity to adjust the pH of the composition from about 1.0 to 6.8, 6.9, 7.0 or greater.

Remineralizing Agent

Re-mineralization is also useful for preventing and treating tooth erosion. Re-mineralization occurs when a mineral is added to the teeth to replace mineral components that have been depleted from the teeth. Softened enamel represents the stage of erosion where a remaining scaffold of mineral crystals can still be re-mineralized or re-hardened.[16] Examples of re-mineralization agents include, fluoride, calcium, and/or phosphate. Fluoride enhances re-mineralization of early carious lesion by adsorbing onto the partially dissolved crystal lattice, which attracts calcium and phosphate ions to precipitate.[17] In vitro and in situ studies have shown that a single or repetitive exposure to fluoride month rinse, fluoride gel, or 5000 ppm fluoride toothpaste, could slow down or prevent the erosive process.[18-20] Fluoride, in the presence of calcium and phosphate, shifts the equilibrium surrounding the tooth surface towards re-mineralization.

In some embodiments, the re-mineralization agent comprises a stannous ion or a stannous ion source. Suitable stannous ion sources include without limitation stannous fluoride, other stannous halides such as stannous chloride dihydrate, stannous pyrophosphate, organic stannous carboxylate salts such as stannous foimate, acetate, gluconate, lactate, tartrate, oxalate, malonate and citrate, stannous ethylene glyoxide and the like. In some embodiments, one or more stannous ion sources are optionally present in the total amount of from about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the re-mineralizing agents can be added to the composition at about 0.01%, 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% % w/w, w/v, or v/v.

In some embodiments, the compositions of the present application further comprise an antimicrobial (e.g., antibacterial) agent. In some embodiments, one or more antimicrobial agents are optionally present. In some embodiments, one or more antimicrobial agents are optionally present in the amount of 0.05%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% to about 10% w/w, w/v/, v/v.

In some embodiments, one or more antimicrobial agents are optionally present in the amount of 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5% to about 3% w/w, w/v/, v/v. Some embodiments of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof 0.1%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1%, 1.5%, 2%, 2.5% to about 3% w/w, w/v/, v/v.

In some embodiments, the compositions may comprise adhesion agents; viscosity modifiers; diluents; nonionic, cationic or amphoteric surfactants; foam modulators; humectants; mouth feel agents; sweeteners; flavoring agents; colorants; or combinations of two or more thereof.

The compositions of the present application are applied by the individual patient or the health care provider as an oral care composition, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity (e.g., increase pH, harden enamel, remineralize teeth, etc.). The oral care composition may be in various forms including toothpaste, dentifrice, tooth gel, subgingival gel, mouth rinse or mouth wash, mousse, foam, mouthspray, lozenge, chewable tablet, chewing gum or denture product. In one embodiment, the oral care composition is in a form selected from toothpaste, dentifrice, tooth gel, mouth wash or denture product. The oral care composition may also be incorporated onto strips or films for direct application or attachment to oral surfaces.

In one embodiment, the oral care composition comprises a mouthwash that is applied in two stages. First a therapeutically effective amount of an alkalinizing agent is applied to the teeth so as to raise saliva pH to 7.0 or above; and then a therapeutically effective amount of a re-mineralizing agent is applied to the teeth.

A "therapeutically effective amount" or "effective amount" is such that when administered, the alkalinizing and re-mineralizing results in alteration of the effects of acid in the oral cavity, such as, for example, prevention of tooth erosion or reduction of tooth erosion, re-hardening and re-mineralization of tooth enamel, etc.

The terms "treating" and "treatment" include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing erosion" includes a decrease in erosion and does not require complete alleviation of erosion signs or symptoms, and does not require a cure.

In various embodiments, reducing erosion includes 5%, 10%, 15%, 20%, 25%, 30%, 35%, 40%, 45% or higher decrease in erosion.

In some embodiments, the alkalinizing agent can be applied to the oral cavity for a time of from about 5, 10, 15, 20, 25, 30, 35, 40, 45, 50, 55 to about 60 seconds. The alkalinizing agent can be applied to the oral cavity at a volume of about 5, 10, 15, 20, 25, 30, 35, 40, 45, 50, 55, 60, 65, 70, 75, 80, 85, 90, 95 to a volume of about 100 milliliters (mL).

In some embodiments, the re-mineralizing agent can be applied to the oral cavity for a time of about 5, 10, 15, 20, 25, 30, 35, 40, 45, 50, 55 to about 60 seconds. The re-mineralizing agent can be applied to the oral cavity at a volume of about 5, 10, 15, 20, 25, 30, 35, 40, 45, 50, 55, 60, 65, 70, 75, 80, 85, 90, 95 to a volume of about 100 mL.

In some embodiments, the alkalinizing agent is an alkalinizing mouthwash. The pH of the alkalinizing mouthwash may be 8.0 or greater.

In some embodiments, a kit is provided that may include additional parts along with the dental compositions. The kit may include a first mouthwash (e.g., alkalinizing agent) in a first compartment. The second compartment may include a second mouthwash (re-mineralizing agent) to be used in the oral cavity and other devices for administering it (e.g., calibrated cups, stirrers, etc.). A third compartment may include other procedural supplies, as well as an instruction booklets or links to websites for product information. A cover of the kit may include illustrations of using the dental composition and a clear plastic cover may be placed over the compartments to maintain sterility.

Conditions Associated with Dental Erosion

Patients with certain chronic health conditions have been shown to have significantly higher erosive tooth wear than a control group.[11] Erosive tooth wear from hydrochloric acid when stomach juice is involuntarily regurgitated has been associated with chronic health issues such as in GERD, hiatal hernia, or occur through chronic vomiting like in bulimia nervosa (Schroeder et al., 1995; Valena and Young, 2002; Barron et al., 2003). Prevalence of dental erosion in GERD patients was 24% (Pace et al., 2008). Preventive treatments that can reduce tooth damage from hydrochloric acid erosion will certainly benefit patients suffering from stomach acid regurgitation due to GERD and eating disorders. According to the National Eating Disorders Association, approximately 11 million Americans suffer from eating disorders. The acts of alkalinizing, re-hardening and re-mineralizing are important in treating and preventing dental erosion in patients suffering from these diseases and in need of such treatment. An acidic challenge in a patient suffering from GERDS or bulimia, can cause an undersaturation of salivary salts (calcium, phosphate), which can contribute to the demineralization of tooth structure.[9,10] Delivery of these minerals to the oral environment by self-application through a mouth rinse or tooth cream is a practical approach for patients with acid regurgitation.

EXAMPLES

Studies were conducted to examine the ability of various treatments to increase the hardening of tooth enamel initially softened by hydrochloric acid (HCl). Further studies were conducted to study the hardness recovery of enamel softened by HCl and remineralized in saliva or artificial saliva after rinsing with sodium bicarbonate and fluoride.

Example 1

Investigation of Treatments to Improve Hardness Recovery of Softened Enamel

This in-vitro study investigated the ability of four treatments to increase the hardening of tooth enamel initially softened by hydrochloric (HCl) acid. The treatments utilized products that contain calcium, phosphate, and/or fluoride, and were compared with hardening by saliva alone.
Methods
Extracted human molars were embedded in acrylic resin and polished. Vickers surface hardness (VH) was measured at each stage in the experiment. After $VH_{baseline}$, the teeth were bathed in a 10 mM HCl solution for 10 minutes to mimic regurgitated stomach acid, and $VH_{softening}$ was recorded. The acid-challenged teeth underwent treatment with the following products: 0.05% sodium fluoride mouthrinse (ACT; Chattem, Inc., Chattanooga, Tenn.), 0.4% stannous fluoride gel (Gel-Kam; Colgate-Palmolive, New York, N.Y.), casein phosphopeptide amorphous calcium phosphate (CPP-ACP) (MI-paste; GC America, Alsip, Ill.), fluoridated CPP-ACP paste (MIPlus; GC America, Alsip, Ill.). Deionized water was used as a control. Following treatment, teeth were bathed in human saliva for 1 hour, and $VH_{hardening}$ was recorded. Statistical analysis was performed with ANOVA followed by Student-Newman-Keuls post-hoc tests (p=0.05). VH (mean±standard deviation) are presented in Table 1.
Results

TABLE 1

Vickers Hardness in extracted human molars

|  | $VH_{baseline}$ | $VH_{softening}$ | $VH_{hardening}$ |
|---|---|---|---|
| Control | 376 ± 18$^a$ | 338 ± 20$^b$ | 344 ± 29$^b$ |
| ACT | 360 ± 32$^a$ | 321 ± 32$^b$ | 342 ± 33$^{a,b}$ |
| Gel-Kam | 361 ± 18$^a$ | 325 ± 32$^b$ | 343 ± 25$^{a,b}$ |
| MI-paste | 362 ± 15$^a$ | 325 ± 7$^b$ | 345 ± 20$^c$ |
| MI-Plus | 358 ± 19$^a$ | 327 ± 14$^b$ | 352 ± 29$^a$ |

Figure 1B:
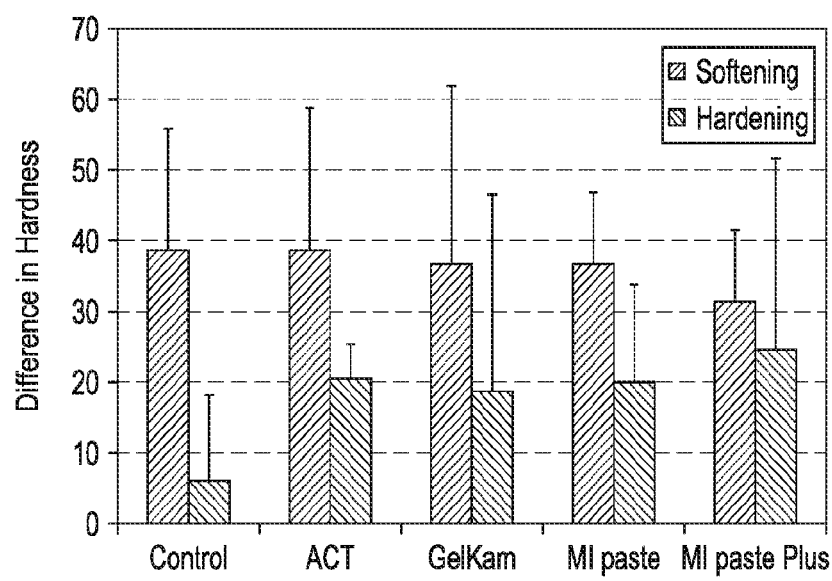

Same superscript letter denotes hardness values that were not significantly different among experimental stages within the same group Now referring to Table 1 and FIGS. 1A and 1B, VH significantly decreased after HCl-challenge in all groups. After re-mineralization, VH increased significantly in MI-paste and MI-Plus groups, but not in the Control, ACT, and Gel-Kam. Only MI-Plus recovered the baseline VH-value.
Conclusion
Hardness recovery of enamel softened by HCl was minimal with saliva alone. The treatment that incorporated fluoride and calcium phosphate was the most effective for enamel hardness recovery.

Example 2

Hardness Recovery after Treatment with Sodium Bicarbonate and Fluoride

In this example, we study the hardness recovery of enamel softened by hydrochloric acid and remineralized in saliva or artificial saliva after rinsing with sodium carbonate and fluoride.
Methods
The effect of acid reflux on enamel was mimicked by immersing extracted human molar in 10 mM hydrochloric acid pH 2.5 for 10 minutes followed by rinsing with tap water or a sodium bicarbonate solution. The re-mineralization phase was carried out by 1 min application of sodium fluoride rinse (ACT) followed by one-hour immersion in artificial saliva containing calcium and phosphate or pooled human saliva (IRB #10-01122-XM). Enamel surface hardness (Vickers) was measured at baseline, softening, and re-mineralization stages. Percent hardness recovery was calculated and subjected to ANOVA followed by Student-Newman-Keuls post-hoc test (p=0.05). N=10. Vickers hardness and percent hardness recovery (mean±standard deviation) are shown in Table 2.
Results

TABLE 2

Vickers Hardness and Hardness Recovery

|  | water rinse + F-rinse/ artificial saliva | Sodium bicarbonate solution + F-rinse/ artificial saliva | water rinse + F-rinse/ saliva | Sodium bicarbonate solution + F-rinse/saliva |
|---|---|---|---|---|
| Baseline hardness | 392 ± 11$^A$ | 388 ± 15$^A$ | 392 ± 13$^A$ | 382 ± 14$^A$ |
| HCl/rinse hardness | 327 ± 21$^B$ | 335 ± 18$^B$ | 315 ± 22$^B$ | 311 ± 21$^B$ |
| Remin hardness | 357 ± 11$^C$ | 369 ± 13$^C$ | 348 ± 11$^C$ | 356 ± 13$^C$ |
| % hardness recovery | 44.9 ± 17.5$^a$ | 67.9 ± 15.4$^b$ | 40.5 ± 14.9$^a$ | 63.6 ± 18.6$^b$ |

Hardness significantly decreased after HCl immersion and significantly increased after re-mineralization in all groups (uppercase superscript letters). Sodium bicarbonate solution plus fluoride rinse significantly increased percent hardness recovery in comparison to water plus fluoride rinse in both artificial saliva and human saliva (lowercase superscript letters).

TABLE 3

Formula for Artificial Saliva

To make 100 mL artificial saliva, combine the following:
100 ml deionized water
0.0221 g 1.5 mM $CaCl_2 \cdot 2H_2O$
0.0122 g 0.9 mM $KH_2PO_4$
0.4766 g 20 mM HEPES buffer
0.9693 g 130 mM KCl
few drops 1M KOH to adjust to pH 7.0
Formula modified from: Mukai Y, Lagerweij MD, ten Cate JM. Effect of a solution with high fluoride concentration on re-mineralization of shallow and deep root surface caries in vitro. Caries Res 2001; 35: 317-324.

Conclusion

The sodium bicarbonate solution and fluoride rinse improved the hardness recovery of enamel softened by hydrochloric acid.

Example 3

Buffering Capacity of Saliva in the Presence of HCl, and the Effectiveness of Sodium Bicarbonate in Neutralizing Acidic Saliva Dental erosion is caused by direct contact of intrinsic or extrinsic acid exposure to natural tooth enamel. Highly acidic gastric juices (pH 1.0-3.0) are present in the saliva of patients suffering from Anorexia or Bulimia. The pH of the mouth may drop from a neutral pH of 6.8 or 7.0 to as low as 2.5 to 3.0. Patients suffering from Bulimia may rummage several times a day causing damage of their natural tooth structure. In presence of acidic substances in the mouth, the salivary glands increase production of saliva that is the body's natural buffering defense system to neutralize the acid. In a healthy individual with normal salivary flow it may take several hours to neutralize the oral cavity, during these few hours the teeth are exposed to an acidic medium, which accelerates the erosion process. Unfortunately patients suffering from eating disorders, acid reflux, and morning sickness due to pregnancy are usually clinically dehydrated and as a result may have lower than normal salivary flow. This may result in even longer period of time required by saliva to normalize the acidity of the mouth.

The majority of the preventive dental products in the market contain fluoride that provides help in re-mineralization of teeth exposed to an acidic medium. However, none of the commercially available products address the acidity of the Saliva resulting from vomiting with Bulimia, or acid regurgitation in patients with Reflux.

The formulated mouth wash described helps neutralize the saliva first and further helps in re-mineralization by replacing the mineral components depleted after an acidic challenge. The formulated mouth wash contains sodium bicarbonate, *Eucalyptus* oil, arginine and several other components including artificial saliva. The treatment includes a two-step system.

First Step: Neutralize the oral cavity and saliva.

Second Step: Rinse with fluoride, calcium and phosphate mixture to re-mineralize and harden the enamel.

Methods

Figure 2:
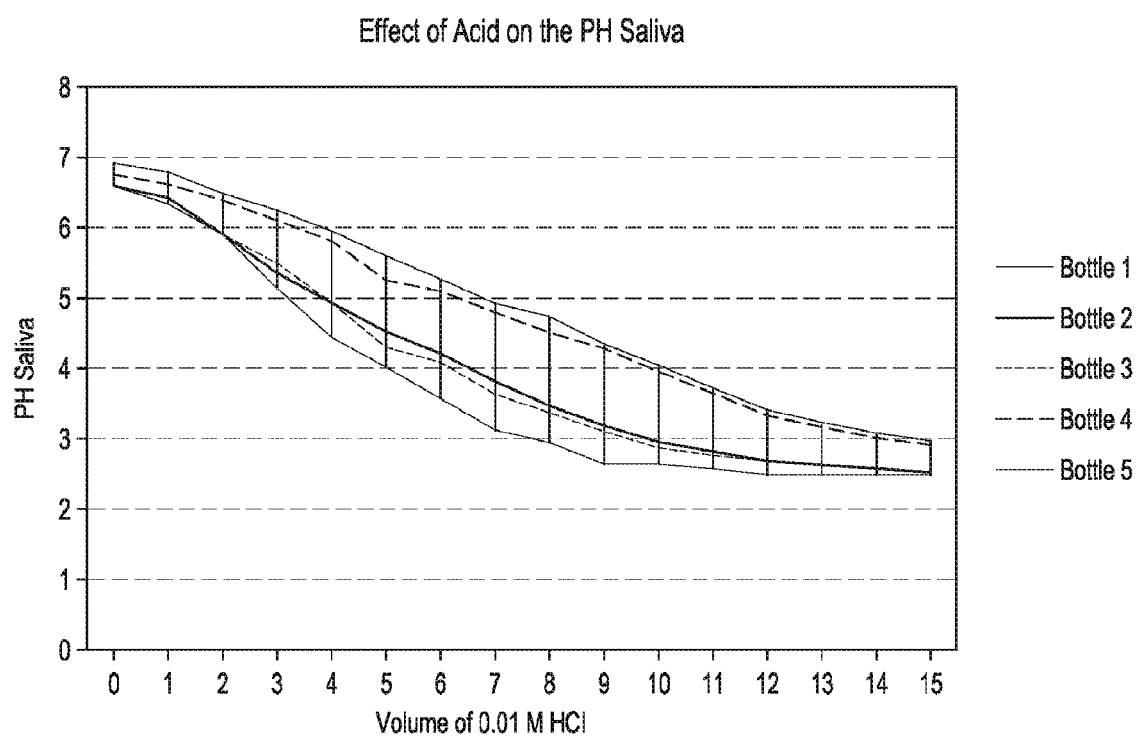
FIG. 2 illustrates the buffering capacity of saliva in the presence of hydrochloric acid.

The capacity of sodium bicarbonate to neutralize acid saliva was assessed. A pool of saliva was collected from 5 individuals, and the normal pH of the saliva was measured before brushing or eating. The average pH of the saliva was 6.8. In order to simulate an acidic challenge, the pH of the saliva was adjusted to 2.5 with 0.01M HCl. FIG. 2 graphically illustrates the effect of the acid on the pH of saliva.

A common recommendation made by dentists to patients suffering from Bulimia is to rinse their mouth with water after an acidic challenge, hoping water will wash away or dilute the acid and the buffering capacity of saliva will neutralize the remaining acid.

The results of this experiment shows that water alone is not effective in increasing the pH of the saliva to the neutral pH of 6.5-7, and the natural buffering effect of saliva is not enough to raise the pH.

Figure 3:
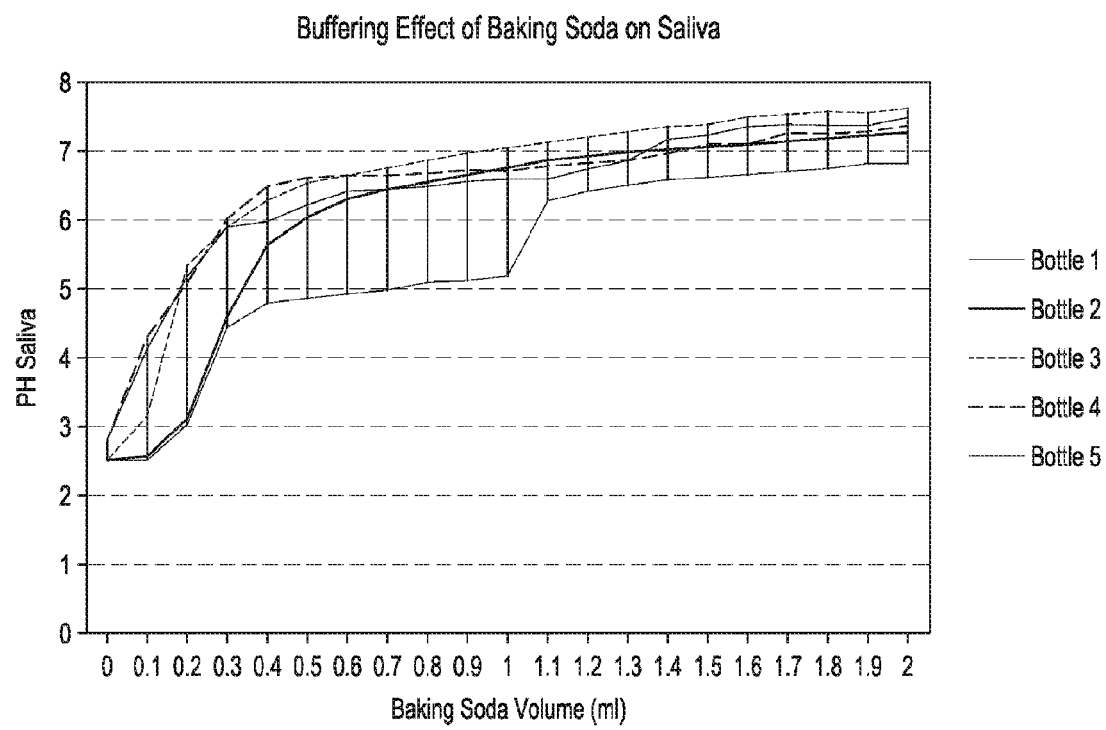
FIG. 3 illustrates the effectiveness of sodium bicarbonate in neutralizing acidic saliva.

The saliva was titrated with a 3M sodium bicarbonate solution and measured the volume of solution necessary to neutralize the saliva to a pH of 6.8. FIG. 3 graphically illustrates the effectiveness of sodium bicarbonate in neutralizing the acidic saliva. Table 4 indicates the amount of 3M sodium bicarbonate that is needed to adjust the pH of the saliva from 2.5 to 6.8 or greater.

TABLE 4

Effectiveness of Sodium Bicarbonate in Neutralizing Acidic Saliva

| Volume Baking Soda | pH Sample 1 | pH Sample 2 | pH Sample 3 | pH Sample 4 | pH Sample 5 |
| --- | --- | --- | --- | --- | --- |
| 0.00 | 2.49 | 2.5 | 2.54 | 2.79 | 2.81 |
| 0.10 | 2.52 | 2.56 | 3.14 | 4.32 | 4.15 |
| 0.20 | 3.07 | 3.1 | 5.31 | 5.12 | 5.18 |
| 0.30 | 4.50 | 4.63 | 5.88 | 6.01 | 5.89 |
| 0.40 | 4.80 | 5.66 | 6.28 | 6.48 | 6.01 |
| 0.50 | 4.85 | 6.05 | 6.52 | 6.58 | 6.23 |
| 0.60 | 4.92 | 6.29 | 6.65 | 6.61 | 6.41 |
| 0.70 | 4.98 | 6.45 | 6.75 | 6.65 | 6.44 |
| 0.80 | 5.08 | 6.58 | 6.85 | 6.67 | 6.5 |
| 0.90 | 5.12 | 6.67 | 7.02 | 6.7 | 6.56 |
| 1.00 | 5.19 | 6.77 | 7.06 | 6.72 | 6.57 |
| 1.10 | 6.28 | 6.86 | 7.13 | 6.77 | 6.59 |
| 1.20 | 6.43 | 6.9 | 7.21 | 6.78 | 6.73 |
| 1.30 | 6.53 | 6.96 | 7.27 | 6.86 | 6.89 |
| 1.40 | 6.60 | 7.01 | 7.35 | 6.97 | 7.12 |
| 1.50 | 6.61 | 7.08 | 7.4 | 7.09 | 7.22 |
| 1.60 | 6.64 | 7.11 | 7.49 | 7.13 | 7.35 |
| 1.70 | 6.70 | 7.18 | 7.51 | 7.25 | 7.39 |
| 1.80 | 6.73 | 7.2 | 7.56 | 7.3 | 7.4 |
| 1.90 | 6.80 | 7.27 | 7.58 | 7.35 | 7.41 |
| 2.00 | 6.81 | 7.3 | 7.61 | 7.39 | 7.49 |

Figure 4:
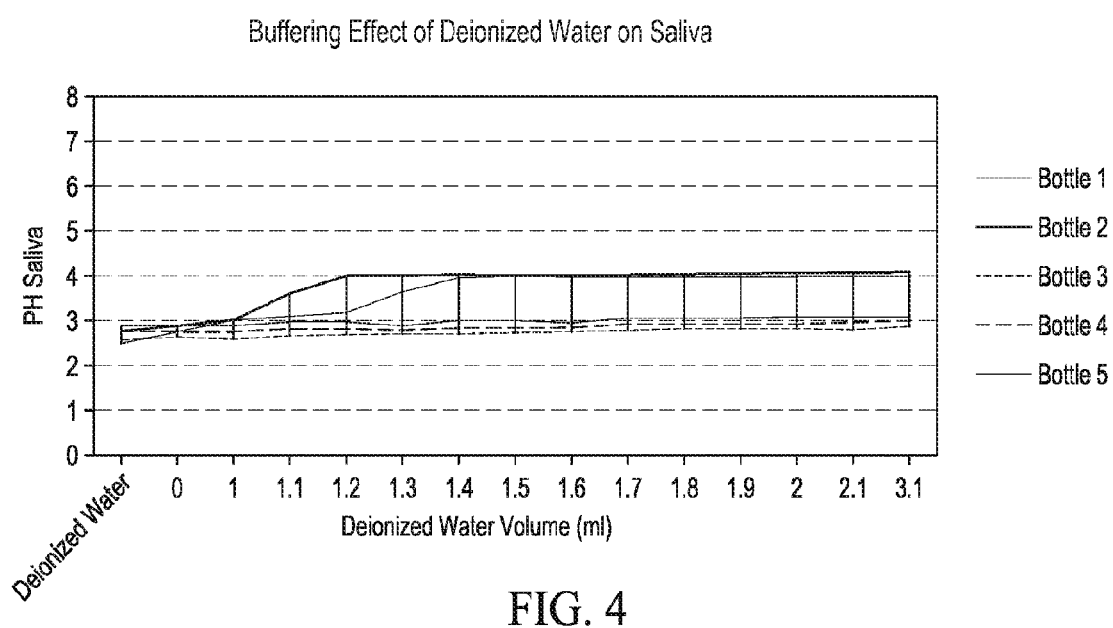
FIG. 4 illustrates the buffering capacity of deionized water on saliva.

FIG. 4 graphically illustrates that water alone is not effective in increasing the pH of the saliva to the neutral pH of 6.5-7, and that the natural buffering effect of saliva is not enough to raise the pH.

These results indicate that acid erosion in the mouth can be prevented and treated by applying an agent capable of neutralizing the acid in the mouth and re-hardening the tooth enamel, and applying an agent capable of re-mineralizing the teeth. Table 5 illustrates the formulation for preventing and treating tooth erosion.

TABLE 5

Formulations for Neutralizing Agent and Re-mineralizing Agent

Neutralizing Agent (Step 1)

| | |
|---|---|
| Sodium Bicarbonate | 0.5-5 wt % |
| Calcium phosphate component | |
| Calcium Chloride | 0.01-0.1 wt % |
| Potassium Phosphate | 0.005-0.05% |
| Arginine Bicarbonate | 1-8 wt % |
| Eucalyptus oil | 1 drop |
| Licorice root extract | 1 drop |

Re-mineralizing Agent (Step 2)

| | |
|---|---|
| Casein phosphopeptide, amorphous calcium phophate | 0.1-10 wt % |
| Sodium Fluoride | 0.01-1 wt % |
| Green Tea Extract | 50-400 mg/mL |

Discussion

As can be seen above, only 2.0 mLs of a 3M solution of sodium bicarbonate is needed to neutralize the acidic saliva to a pH of 7.0. We hence decided in order to combat acid erosion in the mouth we needed to approach it from two directions.

First Neutralize the Acid by a Solution Containing:
1. Sodium bicarbonate, shown in our research to buffer and neutralize the acid
2. *Eucalyptus* oil, flavoring agent
3. 1 to 8% Arginine solution, natural protein present in saliva. It helps in buffering acidic pH.
4. Calcium phosphate, present in artificial saliva. It has been shown to increase microhardness of enamel in our research data.
5. Licorice root extract, acting as a salivary and gustatory stimulant, and a natural antibacterial remedy.

The results of our research shows that rinsing with a sodium bicarbonate solution for 30 seconds is sufficient to help neutralize the saliva; and furthermore eliminate the horrific taste that patients experience as a result of acidic vomitus or acidic regurgitation.

In our experience, patients that experience the horrific taste of acid regurgitation and vomitus are more than willing to use a two step mouth wash, if it can help them eliminate the taste and esophageal burn and discomfort one experiences after throwing up. One of the biggest mistakes patients make after an acidic challenge is to brush their teeth, in order to get rid of the acidic taste of vomitus. Brushing immediately after an acidic regurgitation can be an important factor to further deteriorate enamel as a result of erosion-abrasion caused by the friction and wear between toothbrush bristles incorporating acid into enamel.

Second Remineralize the Enamel by Rinsing with Solution in Step 2, that Contain the Following Ingredients:
1. CPP-ACP (Casein phosphopeptide, derived from casein protein in milk, and amorphous calcium phosphate).
2. Fluoride, 0.05% NaF (230 ppm)
3. Green Tea Extract, shown to increase microhardness in dentin and enamel, and also have anticarious properties;

Formulation for the Two Step Neutralizing Mouth Wash

Step One: Combination of the following
1. Baking soda
6.24 g baking soda (equivalent to 1 teaspoon) in 240 ml water (2.6%)
Range: 0.5-5%
2. 1 drop of *Eucalyptus* oil in 240 ml water
3. 1 to 8% Arginine solution (Arginine Bicarbonate)—4 to 30 grams
4. Calcium phosphate component ('artificial saliva')
1.5 mM $CaCl_2.2H_2O$; Range: 0.5-5 mM
0.9 mM $KH_2PO_4$; Range 0.1-5 mM
5. Licorice root extract Step Two: Combination of the following
1. CPP-ACP (Recaldent)
Casein phosphopeptide, derived from casein protein in milk, Amorphous calcium phosphate Range: 0.1-10%
2. Fluoride
0.05% NaF (230 ppm F)
Range: 0.01-1%
3. Green Tea Extract:
Range 50 mg/ml, 100 mg/ml, 200 mg/ml, 300 mg/ml and 400 mg/ml)

Instructions:
Rinse with step one for 30 seconds, spit and rinse with step two for 30 seconds and spit. The patient should not eat or drink for 30 minutes following treatment.

Example 4

Investigation of Treatment Options to Minimize the Effects of Acid Erosion on Enamel Introduction:

Acid erosion of teeth is a significant oral health problem that has become more prevalent in the recent years due to the popularity of diets high in acidic contents, increase in use of medication causing low salivary flow and systemic conditions such as GERD and bulimia Erosive tooth wear is a form of chemical tooth loss that causes enamel dissolution without involvement of bacterial origin (1). Erosive tooth wear can cause significant tooth damage compromising the esthetics and function of teeth. It no longer affects only the elderly population, and can manifest in all age groups of our society. The earlier dentists diagnose and recommend a preventive regimen for their patients, the more minimal the long lasting effects of tooth erosion.

According to the World Health Organization, dental erosion is the progressive and irreversible loss of hard tissue that is chemically etched away from the tooth surface by extrinsic and/or intrinsic acids by a process that does not involve bacteria. Erosive tooth wear is a significant oral health problem once it compromises the esthetics and function of natural teeth. Chronic health conditions such as gastroesophageal reflux disease (GERD), hiatal hernia, and bulimia nervosa can cause erosive tooth wear from exposure to hydrochloric acid during involuntary regurgitation of stomach juices (2-4). Prevalence of dental erosion in GERD patients was reported to be 24%, 5 and the National Eating Disorder Association has reported approximately 11 millions Americans suffer from eating disorders (6).

Softening of the enamel surface is an early manifestation of acid erosion. Subsequently, the tooth structures are dissolved layer by layer or by a mechanical insult, resulting in bulk-loss of tooth material. The majority of dentists can recall seeing a patient in their dental office with moderate to advanced erosion and tooth wear present on the lingual and incisal edges of their upper anterior teeth as a manifestation of a systemic condition such as Bulimia and GERDS. The majority of these patients require extensive restorative work to return the teeth to optimal function and esthetics.

Case Study: A 46 year old female with a history of acid reflux presented in our office, with extensive erosion on the lingual and incisal edges of her maxillary incisors. The patent informed us that she had been suffering from the symptoms of GERDS for years, but had only recently been placed on medication. She complained of sensitivity on her teeth and was dissatisfied with her smile. Initial examination revealed incisal wear and chipping on the incisal edges, and lingual surface of the upper anteriors, and incisal wear and chipping on the lower anterior teeth. Recurrent decay and occlusal erosion was present on the posterior teeth. Abfraction lesions were present on the facial of teeth #4, #5, #6, #11, #12, #13, #14, #19, #20, and #21. Generalized occlusal wear was present on all teeth.

Treatment: This patient's treatment plan included Empress Veneers on teeth #7 & #10, and Empress Crowns on #8 & #9, porcelain fused to metal crowns on teeth #18, #19, #28, #30, and #31. Incisal composite bonding on the lower anteriors, and class V composites on teeth #4, #5, #12, #13, #20, #21, and #29. An occlusal guard was also treatment planned to stabilize and protect the teeth and prevent damage to the teeth and restorations due to bruxism.

Many patients with dental manifestation of GERDS and bulimia may exhibit more severe tooth destruction, requiring extensive and in some cases full mouth rehabilitation. The ideal scenario for a dentist would be to detect the early signs of erosion in their patients and recommend a preventive regimen in order to minimize and maybe prevent the damage to the dentition from chronic acid exposure.

The most significant natural defense in the oral cavity remains to be saliva, which modulates the severity of erosion by diluting, clearing, and neutralizing the acid, and by supplying the necessary calcium and phosphate ions for re-mineralization.[7] This protective role may not always be sufficient as tooth erosion is evident in a significant number of patients. It may take several hours of re-mineralization to achieve the complete rehardening of softened enamel.8 One contributing factor can be further tooth erosion-abrasion resulting from brushing immediately after an acidic regurgitation.

Various products containing fluoride and/or calcium phosphate are readily available for caries prevention. These products should benefit erosion cases via re-mineralization as well. Fluoride, in the presence of calcium and phosphate, shifts the equilibrium surrounding the tooth surface towards re-mineralization. An acidic challenge in a patient suffering from GERDS or bulimia, can cause an undersaturation of salivary salts (calcium, phosphate), which can contribute to the demineralization of tooth structure. 9,10 Delivery of these minerals to the oral environment by self-application through a mouth rinse or tooth cream is a practical approach for patients with acid regurgitation.

Objectives: This in-vitro study investigated the ability of four treatments to increase the hardening of tooth enamel initially softened by hydrochloric acid, as found in patients with gastric reflux and bulimia. The treatments consisted of products that contain calcium, phosphate, and/or fluoride, and were compared with hardening by saliva alone. Surface microhardness is used to assess enamel softening associated with the initial stage of the erosion process and enamel rehardening to indicate the effectiveness of various preventive treatments.

Materials and Methods

Specimen Preparation—25 extracted human molars (IRB #10-01122-XM) were cut into buccal and lingual halves and embedded in acrylic resin. The teeth were collected from dental clinics in the region and stored in 10% buffered formalin acetate. Buccal and lingual surfaces were free of caries and congenital defects. The enamel surface was ground to achieve a flat surface ca 5×5 mm, using 240, 400 and 600 grit silicon carbide paper, and polished with 1.0 and 0.05 micron alumina suspension before the baseline surface hardness measurement.

Surface Hardness Measurement: Enamel surface hardness was measured with a microhardness tester (Micromet™ 2103, Buehler) using a Vickers indenter at 50 g load for 15 s. Four indentations were performed to obtain an average hardness for each specimen.

Hydrochloric Acid Immersion (Softening stage)—The specimens were immersed in 25 ml of 37 degrees C. 10 mM hydrochloric acid pH 2.5 for 10 mM to mimic an acid challenge from stomach acid regurgitation. The teeth were collected from dental clinics in the region and stored in 10% buffered formalin acetate. Buccal and lingual surfaces were free of caries and congenital defects. The enamel surface was ground to achieve a flat surface, ca 5×5 mm, using 240, 400 and 600 grit silicon carbide paper, and polished with 1.0 and 0.05 micron alumina suspension before the baseline surface hardness measurement. The specimens were then rinsed with 5 ml tap water to simulate a patient rinsing. Surface hardness of the enamel at 'softening' stage was measured after the specimens were dried with compressed air for 30 sec.

Treatments and Saliva Immersion (Rehardening stage)—Resting saliva was collected from five participants in the morning of each day of the experiment and pooled together (IRB #10-01122-XM). The participants were advised not to brush that morning to avoid the influence of toothpaste. One of the following treatments was applied onto the softened enamel surface: 0.05% Sodium fluoride mouth rinse (ACT, Chattem) for 1 mM, 0.4% stannous fluoride gel (Gel-Kam, Colgate Palmolive), casein phosphopeptide amorphous calcium phosphate (CPP-ACP) (Prospec™ MI Paste, GC Corp) for 3 mM, fluoridated CPP-ACP paste (MI Paste Plus, GC Corp) for 3 mM Deionized water was used as a control. After the aforementioned contact time according to manufacturer instructions, the treatments were wiped off and the specimens were immersed in 5 ml of pooled saliva and stored in 37 degrees C. incubator. After one hour, the specimens were rinsed with deionized water, dried with compressed air for 30 sec, and the surface hardness was measured ('rehardening stage'). Sample size was 10 per group.

Data Analysis and Statistical Analysis—Percent hardness reduction from the hydrochloric acid challenge and percent hardness recovery after the treatment and saliva immersion were calculated from the differences in Vickers hardness numbers between the baseline, softening, and rehardening stages. The data was analyzed using ANOVA statistics and Student-Newman-Keuls post-hoc test at a significance level of 0.05.

Results

Vickers hardness values of the enamel surface at different stages of the experiment were obtained. No significant difference in baseline microhardness was found among groups (p>0.05). The hardness significantly reduced after immersion in hydrochloric acid (p<0.05). One-hour immersion in saliva alone did not significantly increase the hardness of softened enamel (p>0.05). Treatment with ACT mouth rinse and Gel-Kam followed by one-hour saliva immersion increased the hardness, but it was not significantly different from the hardness at the softening stage (p>0.05). Hardness of the specimens treated with MI-Paste and MI-Plus followed by saliva immersion increased significantly compared to the softening stage (p<0.05). The hardness values of specimens in the rehardening stage were significantly lower than the baseline hardness values in all groups, except those treated with MI-Plus. Also determined were the percentage of hardness recovery, calculated from the ratio of hardness gain at the rehardening stage and the hardness loss at the softening stage. One-hour immersion in saliva resulted in 16% hardness recovery. Treatment with either fluoride or MI Paste before immersion in saliva improved the hardness recovery to 51-55%. The treatment that combined fluoride and CPP-ACP resulted in a 78% hardness recovery.

Discussion

Preservation of dental hard tissues is at the forefront of dental health care. Considering the implications of tooth erosion associated with chronic health issues like stomach acid regurgitation, prevention is the best service dental professionals can offer to patients. Patients with GERD have been shown to have significantly higher erosive tooth wear than a control group (11). Dental enamel loss caused by tooth brushing abrasion can be minimized by advising patients to avoid brushing their teeth immediately after an acid regurgitation so that saliva can neutralize the acid and remineralize the affected tooth surfaces. However, it is not clear how long a patient should wait, and how much recovery will be achieved even when he/she has normal salivary function.

We chose 10 min immersion in hydrochloric acid pH 2.5 to represent the contact duration of a stomach acid regurgitation episode. This procedure reduced the enamel hardness by approximately 10%, which is similar to the values obtained with a cola drink (12). Within the scope of the current in vitro study, a one-hour immersion in saliva could recover 16% of the hardness loss from the hydrochloric acid challenge. Another in vitro study showed that enamel softened by citric acid could achieve complete rehardening after 6 hours re-mineralization in artificial saliva (8). Others reported 30% and 60% hardness recovery of bovine enamels softened by a cola drink after 1 hour and 48 hours exposure to an intraoral environment (13) whereas another in situ study reported only a 3% increase in post-erosion hardness of human enamel after 2 days (14). Jaeggi and Lussi (15) suggested a waiting period of one hour before tooth brushing after an erosive challenge, which reduced toothbrush abrasion approximately 24%, whereas a half-hour waiting period reduced abrasion 13%. In addition to the inconsistent recovery, such a prolonged waiting time is not practical. Hence a preventive treatment to enhance the saliva ability to reharden softened enamel is desirable.

Softened enamel representing the stage of erosion where a remaining scaffold of mineral crystals can still be remineralized or rehardened (16). Fluoride enhances re-mineralization of early carious lesion by adsorbing onto the partially dissolved crystal lattice, which attracts calcium and phosphate ions to precipitate (17). In vitro and in situ studies have shown that a single or repetitive exposure to fluoride month rinse, fluoride gel, or 5000 ppm fluoride toothpaste, could slow down or prevent the erosive process (18-20). In the present study, both fluoride mouth rinse and fluoride gel recovered approximately 50% of the lost hardness in comparison to 16% in the saliva group. Interestingly, the CPP-ACP group hardness recovery was also in the 50% range. Reynolds et al. (21) reported similar re-mineralization for a toothpaste containing either 2% CPP-ACP or 2800 ppm fluoride in an in situ study.

A systematic review based on clinical in situ trials indicated that CPP-ACP could remineralize initial enamel caries lesions (22). Similar to the present study, several in vitro and in situ studies showed that CPP-ACP paste increased the hardness of enamel softened by acid erosion (12, 14, 23). The addition of fluoride enhanced the re-mineralization potential of CPP-ACP in an initial caries lesion and enamel softened by cola drink (14, 21). In the present study, the percentage of hardness recovery in the fluoridated CPP-ACP group was 78% compared to 51-55% in the fluoride mouth rinse, gel, and CPP-ACP paste groups. In addition, only the fluoridated CPP-ACP group regained hardness at the rehardening stage that was not significantly different from the baseline hardness value. This value was not a complete hardness recovery, but it indicates the potential of preventive treatments to reduce the effect of tooth damage from acid erosion and supports the concept of simultaneous fluoride and calcium phosphate application in re-mineralization.

Preventive treatments that can reduce tooth damage from hydrochloric acid erosion will certainly benefit patients suffering from stomach acid regurgitation due to GERD and eating disorders. Until more effective preventive treatments are developed, practical and available products used after an acid reflux episode may help reduce erosion. The current study evaluated the effectiveness for a wide range of such options. Although this study may be limited by its in vitro nature, we have shown that the results of the investigated preventive treatments were similar to studies that used in situ models. Moreover, since the initial stage of tooth erosion is likely to have common characteristics, the demonstrated effectiveness of various preventive treatments can be expected to also benefit the preventive treatment of erosive tooth wear from other causes.

CONCLUSION

Our in vitro study showed that after a 10 minutes exposure of enamel in hydrochloric acid pH 2.5, there was a 10% reduction in enamel hardness. One hour immersion in saliva alone was not adequate to significantly increase the hardness recovery of enamel. However the treatment that combined fluoride and CPP-ACP in conjunction with immersion in saliva resulted in the highest hardness recovery. This recovery could be a result of replenishing salivary salts (calcium and phosphate), which are diminished as a result of an acidic challenge and adding the fluoride to help the re-mineralization of softened enamel. The most effective preventive regimens for a patient suffering from GERDS or bulimia should include immediate use of a fluoride and CPP-ACP treatment and avoidance of tooth brushing following an acidic challenge. Further clinical studies are necessary to determine the effectiveness of these products.

REFERENCES

1. Imfeld T. Dental erosion. Definition, classification and links. Eur J Oral Sci 1996; 104:151-155.
2. Schroeder P L, Filler S J, Ramirez B, Lazarchik D A, Vaezi M F, Richter J E. Dental erosion and acid reflux disease. Ann Intern Med 1995; 122:809-815.
3. Valena V, Young W G. Dental erosion patterns from intrinsic acid regurgitation and vomiting. Aust Dent J 2002; 47:106-115.
4. Barron R P, Carmichael R P, Marcon M A, Sandor G K. Dental erosion in gastroesophageal reflux disease. J Can Dent Assoc 2003; 69:84-89.
5. Pace F, Pallotta S, Tonini M, Vakil N, Bianchi Porro G. Systematic review: gastro-oesophageal reflux disease and dental lesions. Aliment Pharm Ther 2008; 27:1179-1186.
6. National Eating Disorders Association. Statistics: Eating disorders and their precursors. http://www.nationaleatingdisorders.org/uploads/statistics_tmp.pdf. Downloaded Nov. 5, 2012.

7. Zero D T, Lussi A. Erosion—chemical and biological factor of importance to the dental practitioner. Int Dent J 2005; 55:285-290.
8. Eisenburger M, Addy M, Hughes J A, Shellis R P. Effect of time on the remineralisation of enamel by synthetic saliva after citric acid erosion. Caries Res 2001; 35:211-215.
9. Scheutzel P. Etiology of dental erosion—intrinsic factors. Eur J Oral Sci 1996; 104:178-190.
10. Järvinen V K, Rytömaa I I, Heinonen O P. Risk factors in dental erosion. J Dent Res 1991; 70:942-947.
11. Tantbirojn D, Pintado M R, Versluis A, Dunn C, DeLong R. Quantitative analysis of tooth surface loss associated with gastroesophageal reflux disease: A longitudinal clinical study. J Am Dent Assoc 2012; 143:278-285.
12. Panich M, Poolthong S. The effect of casein phosphopeptide-amorphous calcium phosphate and a cola soft drink on in vitro enamel hardness. J Am Dent Assoc 2009; 140:455-460.
13. Kim J W, Jang K T, Lee S H, Kim C C, Hahn S H, Garcia-Godoy F. In vivo rehardening of enamel eroded by a cola drink. ASDC J Dent Child 2001; 68:122-124
14. Srinivasan N, Kavitha M, Loganathan S C. Comparison of the re-mineralization potential of CPP-ACP and CPP-ACP with 900 ppm fluoride on eroded human enamel: An in situ study. Arch Oral Biol 2010; 55:541-544.
15. Jaeggi T, Lussi A. Toothbrush abrasion of erosively altered enamel after intraoral exposure to saliva: an in situ study. Caries Res 1999; 33:455-461.
16. Amaechi, B T, Higham S M. Dental erosion: possible approaches to prevention and control. J Dent 2005; 33:243-252.
17. Featherstone J D C. The Science and Practice of Caries Prevention. J Am Dent Assoc 2000; 131:887-899.
18. Ganss C, Klimek J, Brune V, Schürmann A. Effects of two fluoridation measures on erosion progression in human enamel and dentine in situ. Caries Res 2004; 38:561-566.
19. White A J, Jones S B, Barbour M E, Churchley D R, Gracia L H, Rees G D Inhibition of erosive dissolution by sodium fluoride: Evidence for a dose-response. J Dent 2012; 40:654-660.
20. Ren Y F, Liu X, Fadel N, Malmstrom H, Barnes V, Xu T. Preventive effects of dentifrice containing 5000 ppm fluoride against dental erosion in situ. J Dent 2011; 39:672-678.
21. Reynolds E C, Cai F, Cochrane N J, Shen P, Walker G D, Morgan M V, Reynolds C. Fluoride and casein phosphopeptide-amorphous calcium phosphate. J Dent Res 2008; 87:344-348.
22. Yengopal V, Mickenautsch S. Caries preventive effect of casein phosphopeptide-amorphous calcium phosphate (CPP-ACP): a meta-analysis. Acta Odontol Scand 2009; 67:321-332.
23. Tantbirojn D, Huang A, Ericson M D, Poolthong S. Change in surface hardness of enamel by a cola drink and a CPP-ACP paste. J Dent 2008; 36:74-79.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating erosion of the teeth in a patient in need of such treatment, the method comprising administering a first mouthwash comprising a therapeutically effective amount of an alkalinizing agent to the teeth so as to raise saliva pH to 7.0 or above; and administering a second mouthwash comprising a therapeutically effective amount of a re-mineralizing agent to the teeth, wherein the alkalinizing agent comprises sodium bicarbonate in an amount of about 0.5-5 wt %, calcium chloride in an amount of about 0.01-0.1 wt %, potassium phosphate in an amount of about 0.005-0.05 wt %, and arginine bicarbonate in an amount of about 1-8 wt %; and the re-mineralizing agent comprises casein phosphopeptide in an amount of about 0.1-10 wt %, and sodium fluoride in an amount of about 0.01-1 wt %.

2. A method according to claim 1, wherein the alkalinizing agent further comprises (i) a re-hardening agent, (ii) eucalyptus, and (iii) licorice root.

3. A method according to claim 1, wherein the pH of the saliva is 5 or below before the alkalinizing agent is applied to the teeth.

4. A method according to claim 1, wherein the pH of the first mouthwash is at least 8.0.

5. A method according to claim 1, wherein the first mouthwash is in a quantity of between about 15 mLs to about 60 mLs.

6. A method according to claim 1, wherein the second mouthwash is in a quantity of between about 15 mLs to 60 mLs.

7. A method according to claim 1, wherein the first mouthwash is applied to the teeth first and contacts the teeth for a time between about 20 and about 35 seconds; and then the second mouthwash is applied following the application of the first mouthwash and contacts the teeth for a time between about 20 and about 35 seconds.

8. A method according to claim 1, wherein the alkalinizing agent further comprises eucalyptus oil and licorice root extract; and the re-mineralizing agent further comprises green tea extract.

* * * * *